(12) United States Patent
Duan et al.

(10) Patent No.: US 9,232,909 B2
(45) Date of Patent: Jan. 12, 2016

(54) COMPUTER-IMPLEMENTED SYSTEM AND METHOD FOR DETERMINING THE POSITION OF A REMOTE OBJECT

(71) Applicants: Xiaodong Duan, Pleasanton, CA (US); Guohua Xiao, Plano, TX (US); Xinhong Wang, San Diego, CA (US)

(72) Inventors: Xiaodong Duan, Pleasanton, CA (US); Guohua Xiao, Plano, TX (US); Xinhong Wang, San Diego, CA (US)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 0 days.

(21) Appl. No.: 14/197,232

(22) Filed: Mar. 5, 2014

(65) Prior Publication Data
US 2014/0187907 A1    Jul. 3, 2014

Related U.S. Application Data

(63) Continuation-in-part of application No. 12/753,931, filed on Apr. 5, 2010, now Pat. No. 8,701,677.

(51) Int. Cl.
| | | |
|---|---|---|
| *A61B 5/06* | (2006.01) | |
| *A61B 5/07* | (2006.01) | |
| *G01B 7/14* | (2006.01) | |
| *A61B 1/00* | (2006.01) | |
| *A61B 1/04* | (2006.01) | |
| A61B 19/00 | (2006.01) | |

(52) U.S. Cl.
CPC ............. *A61B 5/062* (2013.01); *A61B 1/00158* (2013.01); *A61B 1/041* (2013.01); *A61B 5/07* (2013.01); *A61B 19/5244* (2013.01); *G01B 7/14* (2013.01); *A61B 19/5212* (2013.01); *A61B 2019/5251* (2013.01)

(58) Field of Classification Search
CPC ........ A61B 1/041; A61B 5/061; A61B 5/062; A61B 5/06; A61B 5/07; A61B 5/073; A61B 5/4238; A61B 5/4255; A61B 5/6861; A61B 2562/162
See application file for complete search history.

(56) References Cited

U.S. PATENT DOCUMENTS

| | | | |
|---|---|---|---|
| 5,997,473 | A | 12/1999 | Taniguchi et al. |
| 7,511,733 | B2 | 3/2009 | Takizawa |
| 7,656,159 | B2 | 2/2010 | Edelstein |
| 7,902,820 | B2 | 3/2011 | Vervaeke et al. |
| 8,052,595 | B2 | 11/2011 | Minai |
| 2004/0097803 | A1 | 5/2004 | Panescu |
| 2005/0261570 | A1 | 11/2005 | Mate et al. |
| 2008/0177178 | A1 | 7/2008 | Aoki et al. |
| 2009/0066321 | A1* | 3/2009 | Edelstein ................. 324/207.24 |
| 2010/0317968 | A1* | 12/2010 | Wright et al. .................. 600/427 |
| 2013/0217962 | A1 | 8/2013 | Date |
| 2013/0225981 | A1 | 8/2013 | Hasegawa |
| 2013/0237809 | A1 | 9/2013 | Hasegawa |
| 2014/0330114 | A1* | 11/2014 | Navab ........................... 600/424 |

* cited by examiner

*Primary Examiner* — Charles A Marmor, II
*Assistant Examiner* — Thaddeus Cox
(74) *Attorney, Agent, or Firm* — Treasure IP Group, LLC

(57) ABSTRACT

The invention provides methods and systems for determining the position of a remote object such as an in vivo medical device such as capsule or probe within a medical patient. Integrated computer and computer executable remote permanent magnetic dipole position and orientation detection system monitors remote object movement. User interface displays remote permanent magnetic dipole location and orientation in a 3-dimensional view. Database stores object position movement in association with time. Magnetic sensor planes detect remote objects with permanent magnetic dipole and generate magnetic field information signal. Computer stores and searches location and posture information use a file.

10 Claims, 13 Drawing Sheets

A is $B_{max}$ for the front detection plane

B is $B_{max}$ for the back detection plane

C is $B_{max}$ for the left detection plane

D is $B_{max}$ for right detection plane

The intersection of Line AB and CD gives the magnetic dipole position O.

A is $B_{max}$ for the front detection plane

B is $B_{max}$ for the back detection plane

C is $B_{max}$ for the left detection plane

D is $B_{max}$ for right detection plane

The intersection of Line AB and CD gives the magnetic dipole position O.

COMPUTER-IMPLEMENTED SYSTEM AND METHOD FOR DETERMINING THE POSITION OF A REMOTE OBJECT

CROSS REFERENCE TO RELATED APPLICATIONS

This application is a continuation in part of U.S. application Ser. No. 12/753,931 filed on Apr. 5, 2010. The US application is incorporated herein by reference.

TECHNICAL FIELD

The invention relates to the use of magnetic fields for determining the position of remote objects. More particularly, the invention relates to computer implemented systems and methods for determining the position of a remote object having a permanent magnetic field, by using magnetic field spatial geometry characterization point analysis derived from externally sensed magnetic field data.

BACKGROUND OF THE INVENTION

Ingestible wireless medical capsules are known in the medical arts. Such capsules telemetrically transmit information to a receiving and recording apparatus located outside the body. The wireless capsule is swallowed and travels through the digestive tract, collecting and transmitting data during the course of its journey. Receiving and recording apparatus is stationed external to the body. In general, after a day or two, the disposable capsule is excreted naturally from the body and the recorded data, such as for example, temperature, pH, pressure, and transit time, may be transferred for analysis and/or storage. It is known in the art to use wireless medical capsules for collecting images by equipping them with cameras, or for delivering doses of medication to general areas of the digestive system by equipping them with drug reservoirs.

The deployment and detection of relatively small probes or sensors for reconnaissance in confined, inaccessible, or remote spaces is useful in many contexts. Determining the position of an object during deployment faces may challenges. In many applications, the target environment may be no more than a few liters in volume. It is sometimes desirable to determine the position of an object, such as a probe or capsule, with as much precision as possible. Remote sensing may be used in many endeavors, such as industrial or medical applications. For example, the currently available wireless capsules used in the medical field are carried by peristalsis through the digestive tract, and the capsule location during the journey is either unknown or only approximately known. Similarly, in non-medical applications, a probe may be carried by fluid flow and/or gravity, through a system of piping or tubing for example, and its position at any given time only estimated. The lack of position information is a drawback of current wireless capsule technology. For example, often a doctor reviewing data from an in vivo capsule does not know the precise location of features indicated by the data, e.g., an image of a gastro-intestinal tumor. Often an additional scoping procedure or even surgery may be required in order to determine the exact location of the problem. In connection with medical devices, some development of magnetic locating techniques has occurred. One approach, exemplified by U.S. Pat. No. 5,558,091 to Acker, is to embed a magnetic sensor in an in vivo capsule, and track the sensor within the body by relating it to magnetic fields external to the body. Although this approach may be useful to some degree, it does not take into account the effect of the earth's magnetic field or the potential interference of additional magnetic fields such as those that may emanate from electrical current and ferromagnetic materials nearby. Another approach, exemplified by U.S. Pat. No. 6,216,028 to Haynor, is to place a magnet on a medical device such as the tip of a probe inserted into the patient, and detect the magnet's field distribution with sensors located on an outside surface of the body. This approach proposes using four magnetic sensors to measure the magnetic field in the x, y, and z axes, and modeling the magnetic tip as a dipole, solving a number of nonlinear equations to determine the position of the magnetic dipole. The complexity of the computations involved requires considerable computing power and/or a significant amount of time to complete. The complexity of this approach also increases the possibility for considerable error.

Systems and methods for accurately determining remote object, such as a locatable wireless capsule or probe would be useful and advantageous in order to accurately match a location with remotely detected images or other parameters such as pH, temperature, pressure values and so forth. It may also provide advantages for accurately guiding the delivery of medications, or for taking biopsies, or for later surgery. In non-medical applications, it may be used for inspecting piping or fluid-handling systems. Used in conjunction with capsules or probes capable of controlled movement, the capability for timely detection of the probe or capsule position would be particularly advantageous. Due to the foregoing and other problems and potential advantages, improved position determining methods and systems using magnetic fields would a useful contribution to the applicable arts.

SUMMARY OF THE INVENTION

One object of the present invention is to collect real-time magnetic field information, to realize real time detection and location of a capsule so that the medical doctors can easily track the progress of the capsule in a human body.

The present invention discloses a computer implemented capsule position and orientation detection system. Said capsule location system comprises a permanent magnetic dipole in a target area, a first and a second sensor planes, surrounding the target area, and a computer and computer executable program, comprising a remote permanent magnetic dipole identification module, a display unit, a storage module and a search module. Said sensor planes comprise a plurality of magnetic sensors. The remote permanent magnetic dipole identification module identifies the position and orientation of remote permanent magnetic dipole and associated target area information by receiving information from the sensors on the sensor planes. The display unit displays the position and orientation of remote permanent magnetic dipole and associated target area information in a two-dimensional map or three-dimensional layout. The storage module stores the position and orientation of remote permanent magnetic dipole and associated target area information from the identification module and assign a file name. The storage module looks up the remote permanent magnetic dipole position data in response to a request of the file name.

The present invention also discloses another computer implemented capsule position and orientation detection system, wherein the system comprises a permanent magnetic dipole in a target area, a non-stationary sensor plane, positioned near the target area, and a computer and computer executable program. The non-stationary sensor plane comprises a plurality of magnetic sensors. The computer executable program comprises an identification module.

The identification module identifies the position and orientation of the remote permanent magnetic dipole and associated target area information in real time, wherein the dipole position is determined from a first maximum magnetic filed of the dipole on the sensor plane in a first position P1 at t1, and a second maximum magnetic filed of the dipole on the sensor plane in a second position P2 at t2, and wherein the distance between the centers of the sensor plane in P1 and P2 is at least 10 cm, and the magnetic dipole in the target area moves less than 1 mm in the time duration from t1 to t2.

The invention offers a simplified system and method for determining the location of a remote object having a permanent magnetic dipole, with improved positioning accuracy, and relatively rapid position determination. These and other advantageous, features, and benefits of the invention can be understood by one of ordinary skill in the arts upon careful consideration of the detailed description of representative embodiments of the invention in connection with the accompanying drawings.

BRIEF DESCRIPTION OF THE DRAWINGS

The present invention will be more clearly understood from consideration of the description and drawings in which.

Figure 1:
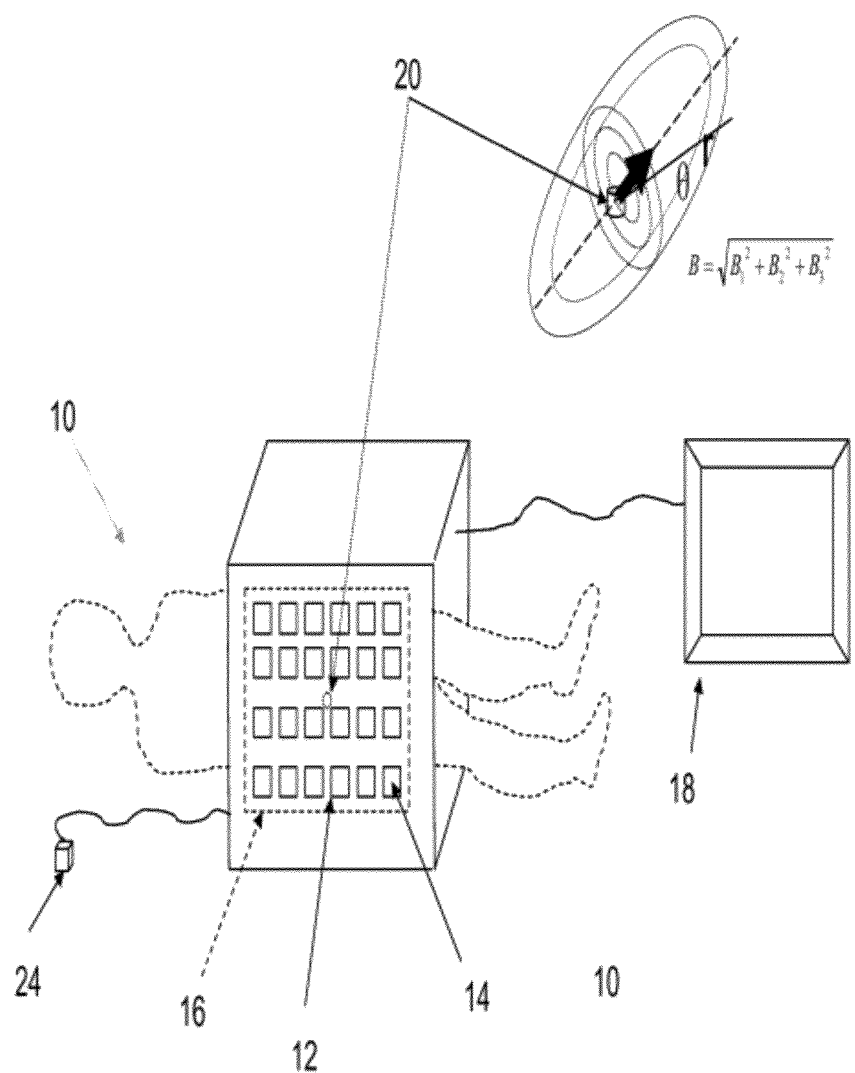
FIG. 1 is a conceptual block diagram providing an overview of a system and method for determining the position of a remote capsule in accordance with one embodiment of the present invention.

References in the detailed description correspond to like references in the various drawings unless otherwise noted. Descriptive and directional terms used in the written description such as front, back, top, bottom, upper, side, et cetera, refer to the drawings themselves as laid out on the paper and not to physical limitations of the invention unless specifically noted. The drawings are not to scale, and some features of embodiments shown and discussed are simplified or amplified for illustrating principles and features as well as advantages of the invention.

DESCRIPTION OF PREFERRED EMBODIMENTS

While the making and using of various exemplary embodiments of the invention are discussed herein, it should be appreciated that the systems and methods exemplify inventive concepts, which can be embodied in a wide variety of specific contexts. It should be understood that the invention may be practiced in various applications and embodiments without altering the principles of the invention. For purposes of clarity, detailed descriptions of functions, components, and systems familiar to those skilled in the applicable arts are not included. In general, the invention provides systems and methods for determining the position of a remote object, for example, an encapsulated probe such as an in vivo medical device, or a probe deployed within a fluid-handling system of piping or tubing. The invention is described in the context of representative example embodiments. Although variations on the details of the embodiments are possible, each has advantages over the prior art due at least in part to increased efficiency realized by performing fewer and/or less complex computations.

In carrying out the principles of the present invention, in accordance with preferred embodiments, the invention provides advances in the arts with novel methods and apparatus directed to detecting and determining the position of a remote object, such as a capsule or probe, deployed within a target area by sensing its magnetic field in one or more planes. The invention may be used with objects, including but not limited to capsules and probes interchangeably, provided that the tracked object includes a permanent or electrical magnet. Thus, the terms capsule and probe are used interchangeably herein unless noted. In addition, in the embodiments of the present invention the capsule is used in a in vivo environments, however the systems and methods disclosed in the present invention can be used for detecting the location of a remote magnetic dipole and its orientation in any enclosed and semi-enclosed area.

Sensor Plane and Detection Plane

In the present invention and written description, a sensor plane means an actual physical plane the sensors are attached onto or embedded in. A detection plane is a virtual plane that the sensors form at a given time. In some examples, the sensor plane is the detection plane. In another examples, the detection plane was a previous position of the sensor plane. In still another examples, the detection planes have planar surface whereas the sensor plane has a curved surface.

Fixed Sensor Planes and Non-Stationary Sensor Planes

In the present invention, the system and methods can be used for either the sensor plane is stationary or non-stationary. The sensor planes in the scope of the present invention can have additional structure units provide either support or mobility. In one example, the sensor plane has a base and the magnetic sensor plane is supported by the based on the ground. In another example, magnetic sensor plane is connected to robotic arm, wherein the robotic arm can move the sensor plane around. In still another example, the magnetic sensor plane is supported by a track or convey belt, wherein the magnetic sensor plane can moves in a linear direction to adjust the position with respect to the target area.

Shape of Sensor Planes

In accordance with the aspect of the present invention, the sensor plane can be in any shape or geometry. In one exemplary embodiment, the sensor plane is a planar structure having a flat surface. Optionally the flat plane can have curvature peripherals. In another exemplary embodiment, the sensor plane is a flat plane with substantially an oval shape. In another example, the sensor plane has a flexible surface. Sensors on the flexible surfaces form virtual and arbitrary detection planes, which can detect the location and orientation of the remote magnetic dipole according to the principles described in the present invention.

Sensor Layout on a Sensor Plane

The magnetic sensors in the present application can be any kind of sensors. In one example, the magnetic sensor is having a size of 2 mm×2 mm. In another example, the magnetic sensor employed in the present invention can detect the magnetic field more than 0.1 Gauss with a spatial resolution of 0.5 mm or higher.

Figure 2:
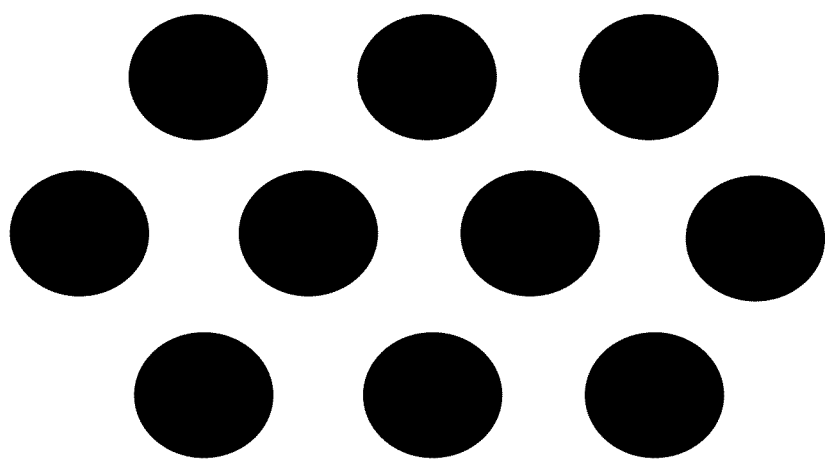
FIG. 2 is a schematic layout of one exemplary sensor plane.

The sensors in the magnetic plane can be arranged in any manner. In one example, the magnetic sensors are arranged as a sensor array as shown in FIG. 1, wherein the sensors are arranged in regular spaced columns and rows. The numbers of sensors in a sensor array can be tailored to a specific application. For instance, the sensor array can be a 10×10 sensor array. In another example, the sensors are arranged in a staggered layout. The individual sensors are arranged either in columns or rows in a staggered fashion to avoid or minimize blind detection spots. One example of such staggered design in one sensor plane is schematically illustrated in FIG. 2, wherein sensors are arranged in three different rows, a first sensor in a first row and a first sensor in a third row is in the same column, but a first sensor in a second row is not in the same column. The distance between one sensor and its closest neighboring sensor is 5 mm apart.

Sensor Detection Limit

Any kind of sensor can be used in accordance with the scope of the present invention. In one example of the present invention, the sensor can detect a magnetic field of 0.01 Gauss when the sensor is placed 0.5 m away from the remote object. In another example of the present invention, the sensor array can detect the location of a remote object with a spatial resolution at least 0.5 to 1 mm.

The sensors in the sensor array disclosed in the present invention can be controlled individually to allow the user to select a plurality of sensors surrounding a maximum magnetic field position in a detection plane. In order to simplify the operation, the sensors in the sensor array can also be controlled in rows or in columns. Users can choose to turn on and off different individual sensors according to their specific need through a user interface on the display.

Capsule, Probe and Remote Object

In the present invention, although the embodiments and examples are directed towards a capsule, or a probe, the systems and methods described herein can also be used to identify location and pasture for any remote object having a permanent magnetic dipole. The capsule, probe or remote object can be used interchangeably with the scope of the present invention.

Wired and Wireless

In the present invention, although embodiments and examples are directed towards a capsule, which is wireless, the systems and methods described herein also can be used for a wired capsule without further undo experimentation.

According to one aspect of the invention, a system for determining the position of a remote object includes a targeted object including its own magnetic field for placement on site, i.e., in situ. The system also includes an external magnetic sensor array configured for sensing the magnetic field of the object, e.g., capsule or probe for example, in one or more planes. Computing apparatus is used for magnetic field spatial geometry characterization point analysis in order to determine the position of the object from the sensed magnetic field.

According to another aspect of the invention, a system for determining the position of a remote object as exemplified in the above embodiment also includes at least one background offset sensor for correcting position data for locally measured magnetic fields.

According to another aspect of the invention, a system for determining the position of a remote object as described herein further includes at least one non-stationary sensor plane.

According to yet another aspect of the invention, an in vivo position determining system for medical use includes a capsule or probe having a magnetic field for placement in vivo. The system also includes, deployed outside the body, an external magnetic sensor array configured for sensing the magnetic field of the capsule in one or more planes, as well as magnetic field spatial geometry characterization point analysis apparatus for determining the position of the capsule in vivo from the sensed magnetic field.

According to another aspect of the invention, a preferred embodiment of a method for determining the position of a remote object includes steps for positioning an external magnetic sensor array for sensing the magnetic field of an object within a target area, and using the sensed magnetic field of the object, determining object position data using magnetic field spatial geometry characterization point analysis.

According to another aspect of the invention, an in vivo position determination method includes the step of placing a capsule comprising a magnetic field within a patient, or in vivo. In further steps, an external magnetic sensor array is located for sensing the magnetic field of the capsule. Using the sensed magnetic field, capsule position data is computed by magnetic field spatial geometry characterization point analysis.

An exemplary embodiment of a system and method for remotely determining the position of an object is shown in the conceptual view of FIG. 1. An operating environment 10 (not part of the invention), such as a medical patient or a confined area such as a mechanical, fluid-handling, or hydraulic system, and at least one sensor array 12 are positioned relative to one another in a configuration further described herein. The sensor array(s) 12 include one or more individual sensor cells 14, preferably uniformly distributed in a sensor plane corresponding with a target area 16 of the operating environment 10. A suitable computer or data processing apparatus 18 is operably coupled to the sensor arrays 12 for performing computations referenced and described herein. A capsule 20, or probe, is preferably deployed inside the target area 16. In the case of a medical implementation, the device may be swallowed by a human or inserted into a veterinary patient, for example. In other implementations, the capsule may be introduced into a system of pipes, a tank or other vessel, mechanical enclosure, or other confined or inhospitable environment where remote sensing or probing is desirable. The capsule 20 includes a dipole magnetic field, preferably generated by a permanent magnet included as a part of the capsule, represented by the diagram inset, and further described by Equation 1. The dipole magnetic field B, is a scalar value (not a vector) wherein m represents the magnetic moment of the magnetic dipole (for the purposes of this description, capsule 20), and wherein r represents distance from the magnetic dipole 20. Angle Θ represents the orientation of the capsule 20 relative to moment and distance. It should be appreciated that the capsule 20 typically also includes devices for gathering one or more data points from its surroundings, such as temperature, pH, pressure, chemistry, charge, imagery, and so forth.

$$B(r, \theta) = \frac{\mu_0 m}{4\pi r^3}\sqrt{1 + 3\cos^2\theta} \quad \text{(Equation 1)}$$

Examples of magnetic field sensor cells 14 include Hall effect sensors, which vary their output voltage responsive to changes in magnetic field, and magneto resistive sensors, which vary their electrical resistance in response to an external magnetic field. The Hall sensor is capable of a greater detection range, whereas magneto resistive sensors are capable of greater sensitivity. Other magnetic sensor types or combinations of sensors may also be used without departure from the invention. A sensor array 12, as shown in the example of FIG. 1, preferably includes multiple sensors in a planar arrangement. Suitable field magnetic sensors on the order of 2 mm×2 mm are commercially available and are presently preferred for in vivo system embodiments. For example, in an array of 2 mm magnetic field sensors spaced 5 mm apart, when the detected magnetic field is 0.01 Gauss, using the systems and methods further described herein, a spatial resolution of 0.5 mm is attainable. Accordingly, the position of the magnetic field, e.g., magnetic dipole or capsule 20 location, may be determined within about 1 mm. In order to scan a target area larger than the sensor array, and/or to reduce the number of sensor cells required in an array, the sensor array may be moved relative to the target area, or vice versa. The magnetic sensor array and/or target area movement is preferably conducted along the plane described by the sensor array, preferably using a mechanical guide to ensure that the correct orientation is maintained and automated or human impelling force.

Preferably, positioning accuracy is enhanced by taking into account an offset magnetic field value when performing positioning computations described herein. A value for the earth's magnetic field, for example, may be stored and applied for correction of calculations made based on magnetic field sensor values indicative of the position of the capsule. Additionally, or alternatively, a magnetic field offset sensor 22 may be used to provide an actual offset value for the particular location and conditions, e.g. the earth magnetic field and the presence of magnetic materials or field-generating electric current. The capsule position data is preferably corrected using the magnetic field offset data. The magnetic field offset sensor 22 is preferably positioned so that it will not sense the magnetic field of the capsule 20, and bears a known, preferably constant, spatial relationship to the magnetic field sensor cells 14 of the magnetic field sensor array 12.

Now referring primarily to FIG. 2, a preferred embodiment of a system and method is shown, in which a target area 16 is encompassed within four magnetic field sensor planes, denominated 12A, 12B, 12C, and 12D. Preferably, the sensor planes are configured in sets of two parallel planes. As shown in FIG. 2, front plane 12A is parallel to back plane 12B, and left plane 12C is parallel to right plane 12D. Preferably, the maximum magnetic field point is determined by magnetic field sensor readings on each plane, indicated in FIG. 2 by points A, B, C, and D, respectively. The maximum points on the opposing planes are used to define lines AB and CD. The intersection of the lines indicates the point X within the target area 16 at which the magnetic field is strongest, thus giving the capsule 20 position in three-dimensional space. Preferably, a magnetic field offset is applied to correct the position information based on what is known about magnetic fields present in the operating environment, such as the earth's magnetic field and/or additional locally detected magnetic fields. Those skilled in the arts should note that this particular embodiment does not require data concerning the magnetic field direction; no magnetic moment value is needed. The method and system described in this embodiment offers advantages in efficiency, requiring reduced computation and processing time, and/or reduced complexity relative to the prior art.

Figure 3:
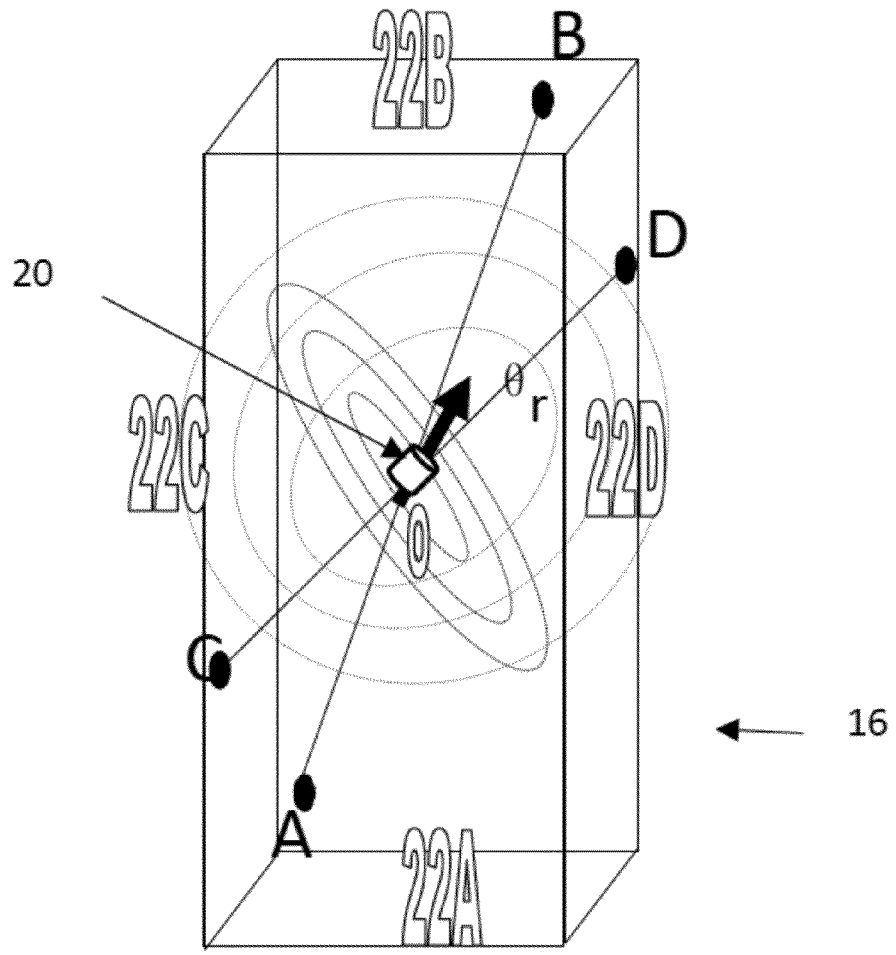
FIG. 3 illustrates an example of an alternative preferred embodiment of a position determination system and method in which four stationary magnetic field sensor planes are used.

In another preferred embodiment, illustrated in FIG. 3, the position of the capsule 20 may be determined using two sensor planes, denoted 12E and 12F. The sensor planes 12E, 12F, are preferably parallel. The maximum magnetic field points, E, F, and the magnetic field vector are used to determine the dipole location and orientation. Referring to Equations 2-7, the moment of the magnetic dipole is related to the magnetic field. The dipole magnetic moment m is derived from the dipole moment along line AB and perpendicular to line AB. (Equations 1-2). The magnetic field at point A can be derived from the magnetic field along line AB, and perpendicular to line AB. The same can be done for point B. The magnetic fields of the dipole are preferably computed as shown in Equations 3 and 4. Since the magnetic fields along the x, y, and z axes are measured at the magnetic field sensor cells, the line AB perpendicular and parallel component values can be calculated with the measurement data. Thus the dipole position, point X, can be calculated (Equation 5), and the angle θ can be derived. (Equation 6). The dipole's perpendicular orientation is the same as the line AB perpendicular magnetic field component, thus the dipole orientation can also be determined. It should be noted that the two parallel planes may alternatively be located on the same side of the dipole without departure from the invention, since the line between their maximum points, e.g., line AB, would nevertheless be established.

$$\vec{m} = \vec{m_{AB\parallel}} + \vec{m_{AB\perp}} \quad \text{(Equation 2)}$$

$$\vec{m_{AB\parallel}} = m\cos\theta, \; \vec{m_{AB\perp}} = m\sin\theta \quad \text{(Equation 3)}$$

$$B_{A\_ABP} = \frac{\mu_0 m_{ABP}}{2\pi r_{OA}^3}, \; B_{B\_ABP} = \frac{\mu_0 m_{ABP}}{2\pi r_{OB}^3} \quad \text{(Equation 4)}$$

$$B_{A\_AB\perp} = \frac{\mu_0 m_{AB\perp}}{2\pi r_{OA}^3}, \; B_{B\_AB\perp} = \frac{\mu_0 m_{AB\perp}}{2\pi r_{OB}^3} \quad \text{(Equation 5)}$$

$$\frac{OA}{OB} = \sqrt[3]{\frac{B_{A\_ABP}}{B_{B\_ABP}}} = \sqrt[3]{\frac{B_{A\_AB\perp}}{B_{B\_AB\perp}}} \quad \text{(Equation 6)}$$

$$\tan\theta = \frac{B_{A\_AB\perp}}{2B_{A\_ABP}} = \frac{B_{B\_AB\perp}}{B_{B\_ABP}} \quad \text{(Equation 7)}$$

Figure 4:
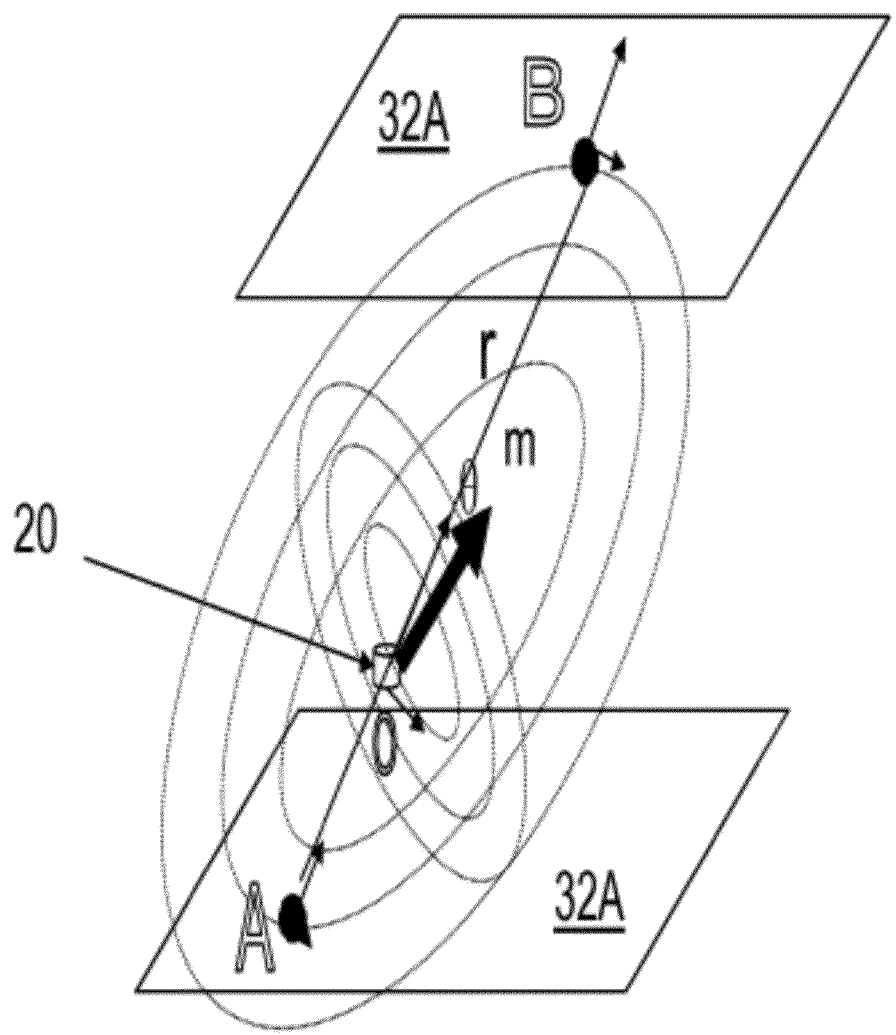
FIG. 4 illustrates an example of an alternative preferred embodiment of a position determination system and method in which two stationary magnetic field sensor planes are used.

In an example of an alternative embodiment of the invention, depicted in FIG. 4, a single magnetic field sensor plane 12 is used to determine the position of the magnetic field of a capsule 20. By the partial differentiation of the magnetic field curve, the maximum field condition is derived. The set of the nonlinear equations, Equations 8-11.6, express the derivation of the dipole location and orientation from the sensed magnetic field.

$$B(x, y, z) = \sqrt{B_x^2 + B_y^2 + B_z^2} = \frac{\mu_0}{4\pi} \frac{1}{r^4} \sqrt{3Q^2 + m^2 r^2} \quad \text{(Eq. 8)}$$

$$Q = [m_x(x - x_0) + m_y(y - y_0) + m_z(z - z_0)]$$

$$r = \sqrt{(x - x_0)^2 + (y - y_0)^2 + (z - z_0)^2}$$

$$F(x, y, z) = \frac{\mu_0}{4\pi} \frac{1}{r^4} \sqrt{3Q^2 + m^2 r^2} - B \quad \text{(Eq. 9)}$$

$$\left( \frac{\partial F}{\partial x}, \frac{\partial F}{\partial y}, \frac{\partial F}{\partial z} \right) \quad \text{(Eq. 10)}$$

$$\frac{\partial F}{\partial x} = 0, \quad \text{(Eq. 11.1)}$$

$$\frac{\partial F}{\partial y} = 0, \quad \text{(Eq. 11.2)}$$

$$\frac{\partial F}{\partial z} = 1 \quad \text{(Eq. 11.3)}$$

$$B_x = \frac{\mu_0}{4\pi} \frac{3Q(x - x_0) - m_x r^2}{r^5} \quad \text{(Eq. 11.4)}$$

$$B_y = \frac{\mu_0}{4\pi} \frac{3Q(y - y_0) - m_y r^2}{r^5} \quad \text{(Eq. 11.5)}$$

$$B_z = \frac{\mu_0}{4\pi} \frac{3Q(z - z_0) - m_z r^2}{r^5} \quad \text{(Eq. 11.6)}$$

Assuming for example, that the maximum magnetic field is at point A (0, 0, 0). The equal magnetic field curve Q has a tangent plane (z=0) at A, and the normal line is vector (0, 0, 1). The magnetic field, B(x, y, z) is as shown by Equation 8. The curve Q equation is as represented by Equation 9. The vector of the curve surface is shown by Equation 10. Considering the normal line at the tangent plane at point A permits the derivation of six equations (Equations 11.1-11.6), which can be used to solve for the six unknown parameters, denoted, x0, y0, z0, mx, my, and mz, that represent the magnetic dipole, in this case capsule 20, position and orientation.

Figure 5:
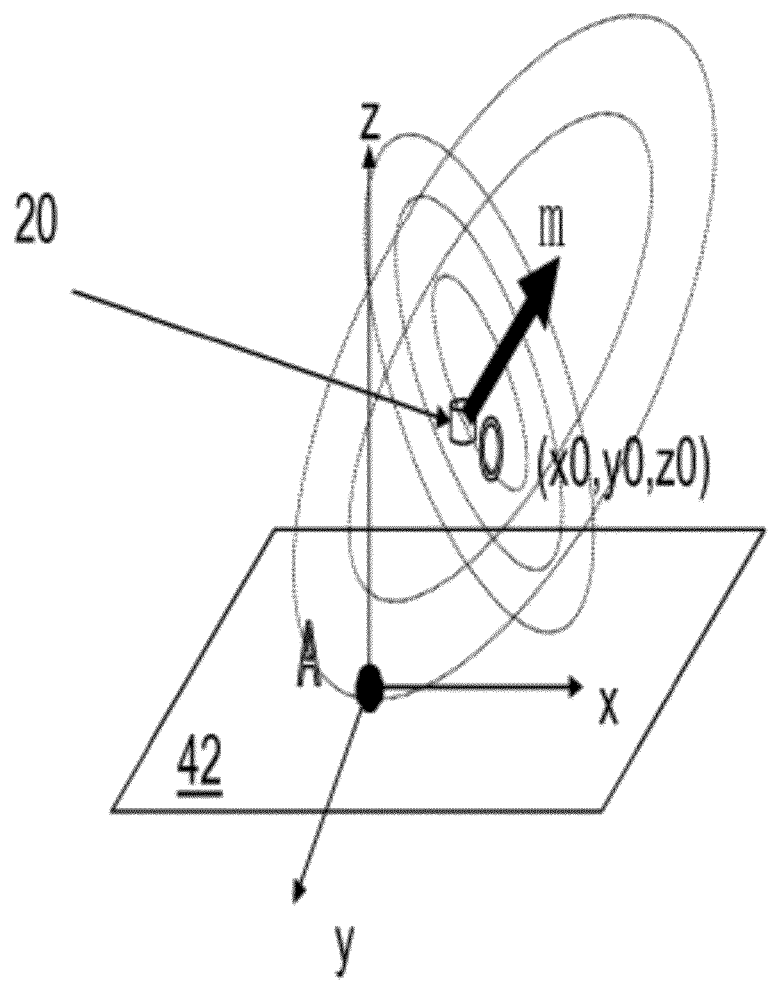
FIG. 5 provides an example of an alternative preferred embodiment of a position determination system and method in which a stationary single magnetic field sensor plane is used.

Referring to FIG. 5, another alternative detection system and method is illustrated, wherein the remote object position and orientation detection system employs a non-stationary sensor planes. Said non-stationery sensor planes can move in either the direction parallel or perpendicular to the human body. In one example, the sensor plane moves along the human body to arrive at the target position. In another example, the sensor plane moves closer to the human body to obtain a stronger magnetic field data.

Unlike the fixed sensor planes depicted in FIG. 1, which requires the patient to be lying down, the non-stationary sensor plane allows the patient to be checked up in different positions such as standing.

The non-stationary sensor planes can be further attached to a ground support with optional wheels, or a robotic arm to make it into a standalone unit. The non-stationary sensor planes can be also made into a vest that a patient can wear during the checkup.

Figure 6:
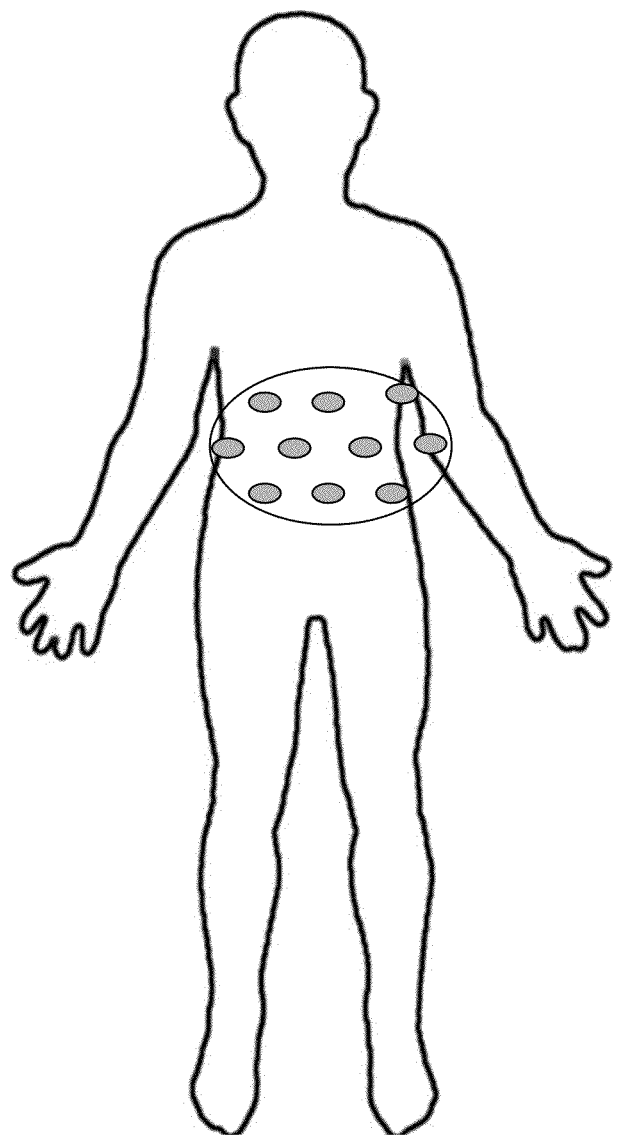
FIG. 6 is a conceptual block diagram providing an overview of a system for determining the position of a remote capsule wherein a non-stationary magnetic plane is employed, in accordance with one embodiment of the present invention.

Referring to FIG. 6, one non-stationary sensor plane can accomplish the same measurements in locating a magnetic dipole as four fixed sensor planes using the method described above and illustrated in FIG. 3, as long as the movement of the magnetic dipole at given test period can be ignored. In one example, the non-stationary sensor plane detects a first maximum point (for example A) on a first detection plane then moves to find a second maximum point (for example B) on a second detection plane. The non-stationary sensor plane moves until all four maximum position points (for example A, B, C, and D) are located. The magnetic dipole position can be determined by the intersection of lines between maximum points on opposing detection plane. In FIG. 6, the current detection plane at a given time is drawn in straight line and the dotted lines denote a reference detection plane to illustrate the environment.

Figure 7:
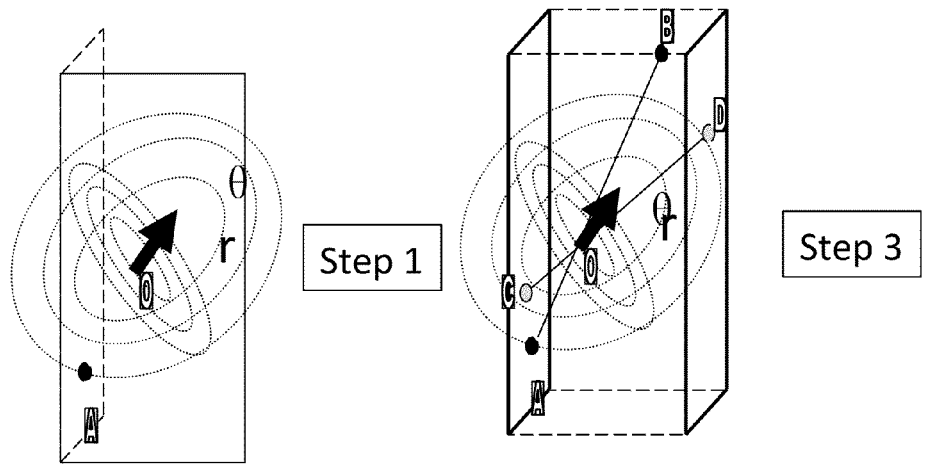
FIG. 7 provides an example of an alternative preferred embodiment of a position determination system and method in which a non-stationary single magnetic field sensor plane is used.
Figure 7:
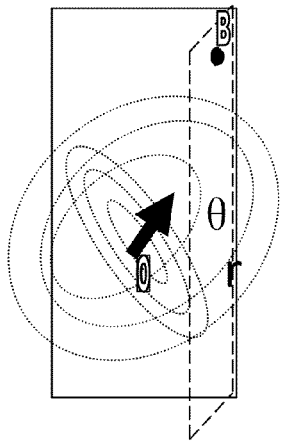

Referring to FIG. 7, one non-stationary sensor plane can perform the same tests in locating a magnetic dipole as four fixed sensor planes using the method described above and illustrated in FIG. 3, as long as the movement of the magnetic dipole at given measurement period can be ignored. The non-stationary sensor plane detects a first maximum point (for example A) on a first detection plane then moves to find a second maximum point (for example B) on a second detection plane. After the non-stationary sensor plane find both maximum position points (for example A, and B) on the two detection planes, the magnetic dipole position can be determined by the method described above and FIG. 3.

Further, one non-stationary sensor plane can also be used in conjunction with fixed sensor planes.

Figure 8:
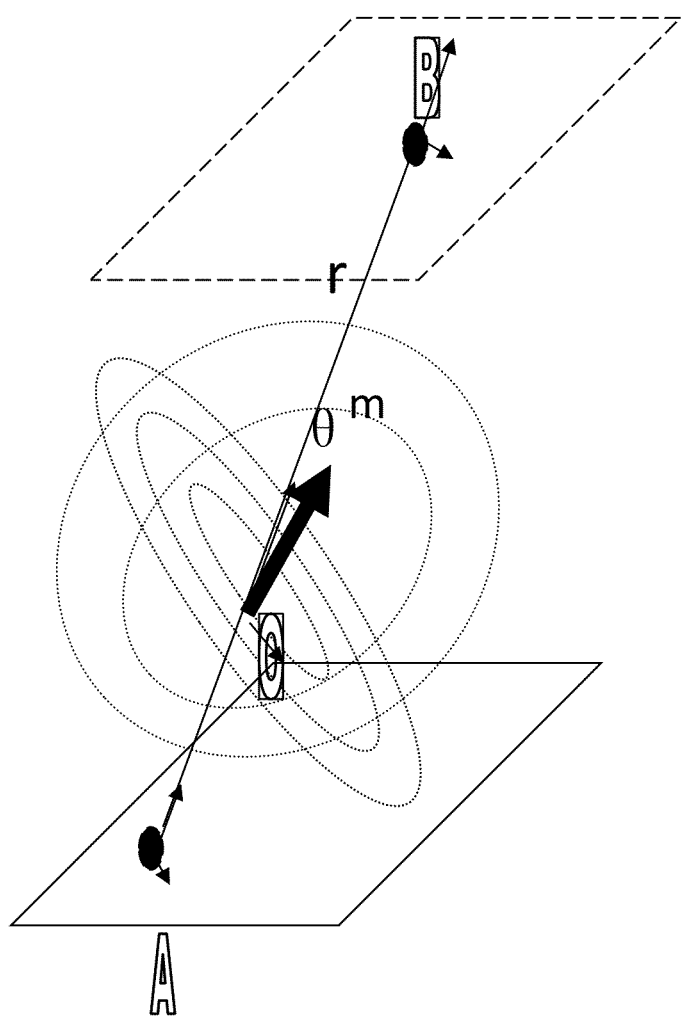
FIG. 8 provides an example of another alternative preferred embodiment of a position determination system and method in which a non-stationary single magnetic field sensor plane is used.

FIG. 8 depicts another alternative remote object position and orientation detection system, wherein more than one non-stationary sensor planes are employed. A first non-stationary sensor plane can be used to sense the magnetic field on the front and back of a patient. A second non-stationary sensor plane can be used to sense the magnetic filed on the left and right of the patient. The position and orientation of the magnetic field can be derived by the method described above as in FIG. 3 or FIG. 6.

The non-stationary sensor plane described in the present invention offers less expensive alternatives to the fixed sensor planes detection systems, without losing the efficiency, particularly for making time-sensitive position determinations, such as, for example in systems equipped for real-time sensing and/or controlled movement of a capsule or probe.

The present invention further discloses a computer and computer executable programs for a capsule position and orientation detection system. The computer and computer executable programs for locating a capsule comprises a remote permanent magnetic dipole identification module, and a display unit and a storage module.

The magnetic dipole identification module communicates with a plurality of magnetic sensors on a sensor plane and receives the magnetic field information from the magnetic sensors, directly or indirectly. In one example, the magnetic dipole identification module communicates with the magnetic sensors through communication devices. Any commercial available wired or wireless communication device can be used for this application.

The magnetic dipole identification module receives the magnetic field data from the sensors on the sensor plane through a USB adapter, process the magnetic filed data and calculate the position and orientation of the remote object, and subsequently send to a display module for display. The storage module stores the position and orientation data of remote permanent magnetic dipole and associated target area information from the identification module and assign a file name. The associated target area information includes time information. The computer and computer executable programs for locating a capsule further comprises a search module looks up the remote permanent magnetic dipole position data in response to a request of a file name.

The display unit displays the position and orientation of remote permanent magnetic dipole and associated target area information in either a two-dimensional map or three-dimensional view. The storage module stores the position and orientation of the remote magnetic dipole and associated target area information from the identification module and assign a file name.

In accordance with the aspects of the present invention, the location of the capsule is determined by first finding a maximum magnetic filed position on a sensor plane.

Figure 9:
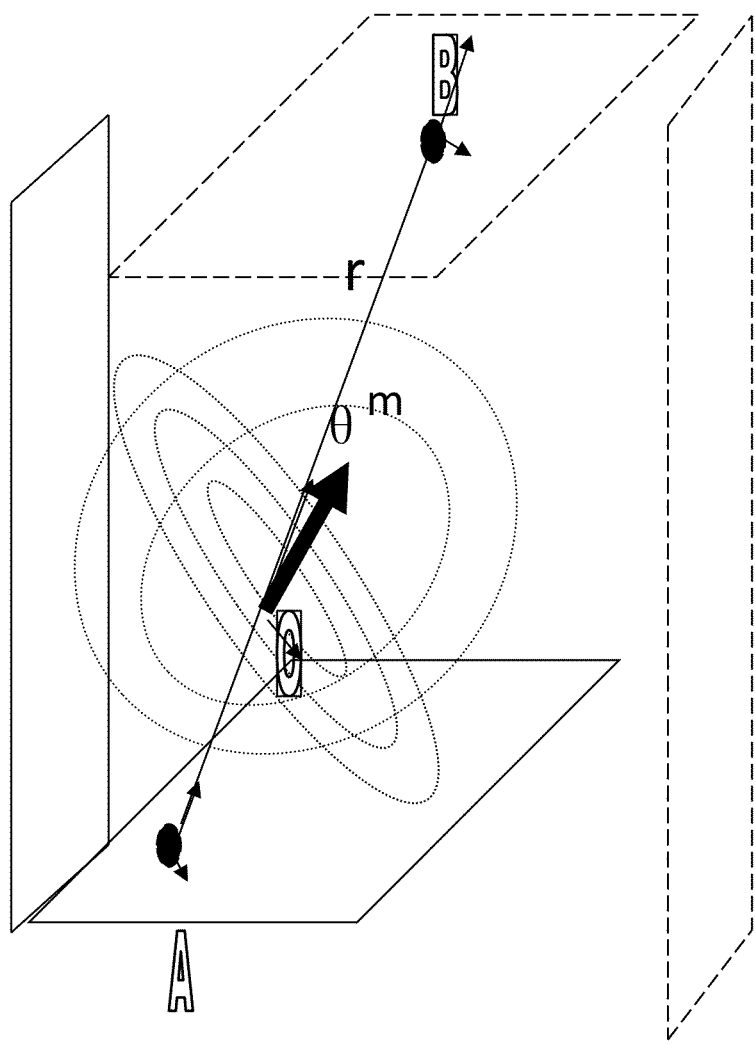
FIG. 9 provides an example of another alternative preferred embodiment of a position determination system and method in which a non-stationary single plane is used.

In one embodiment of the present invention, referring to FIG. 9, the sensor plane comprising magnetic sensors further comprises an electrical board, and the sensor plane is connected to nRFLE1 by I2C. In one example as illustrated in FIG. 9, the location of the capsule is sensed by two sensor planes, two sensor planes are connected to nRFLE1 in parallel.

Figure 10:
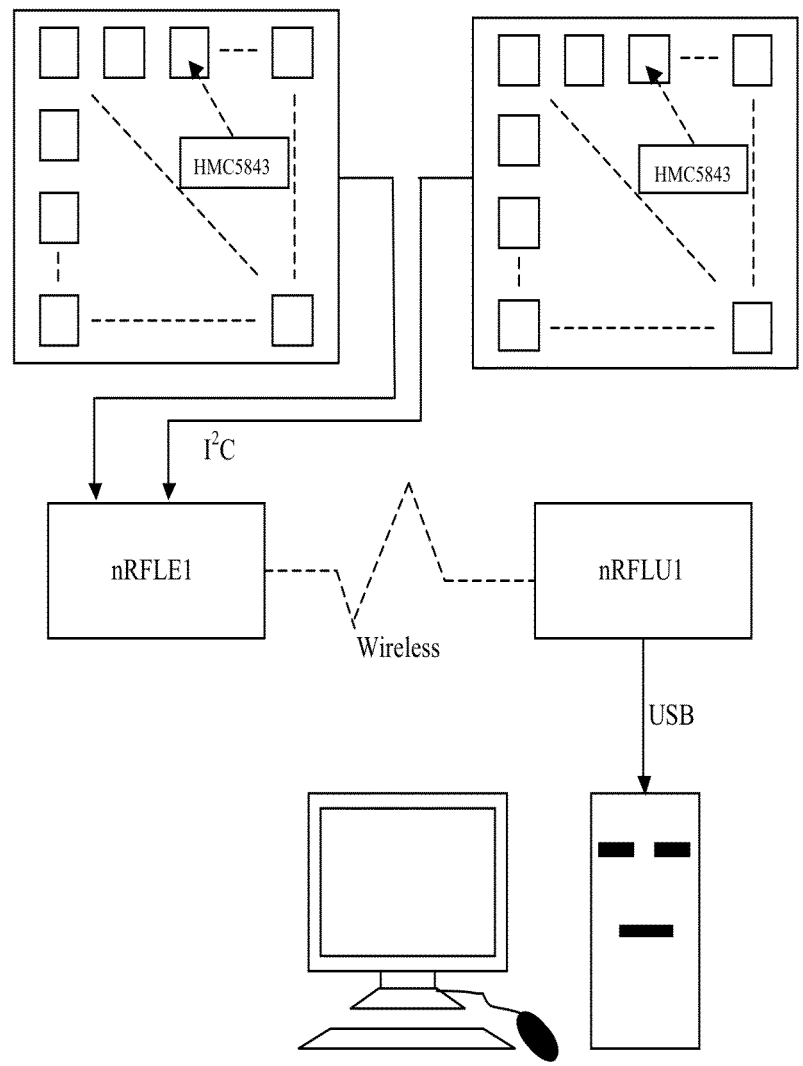
FIG. 10 illustrates a schematic diagram of a capsule position determination system, in accordance with the aspect of the present invention.
Figure 11:
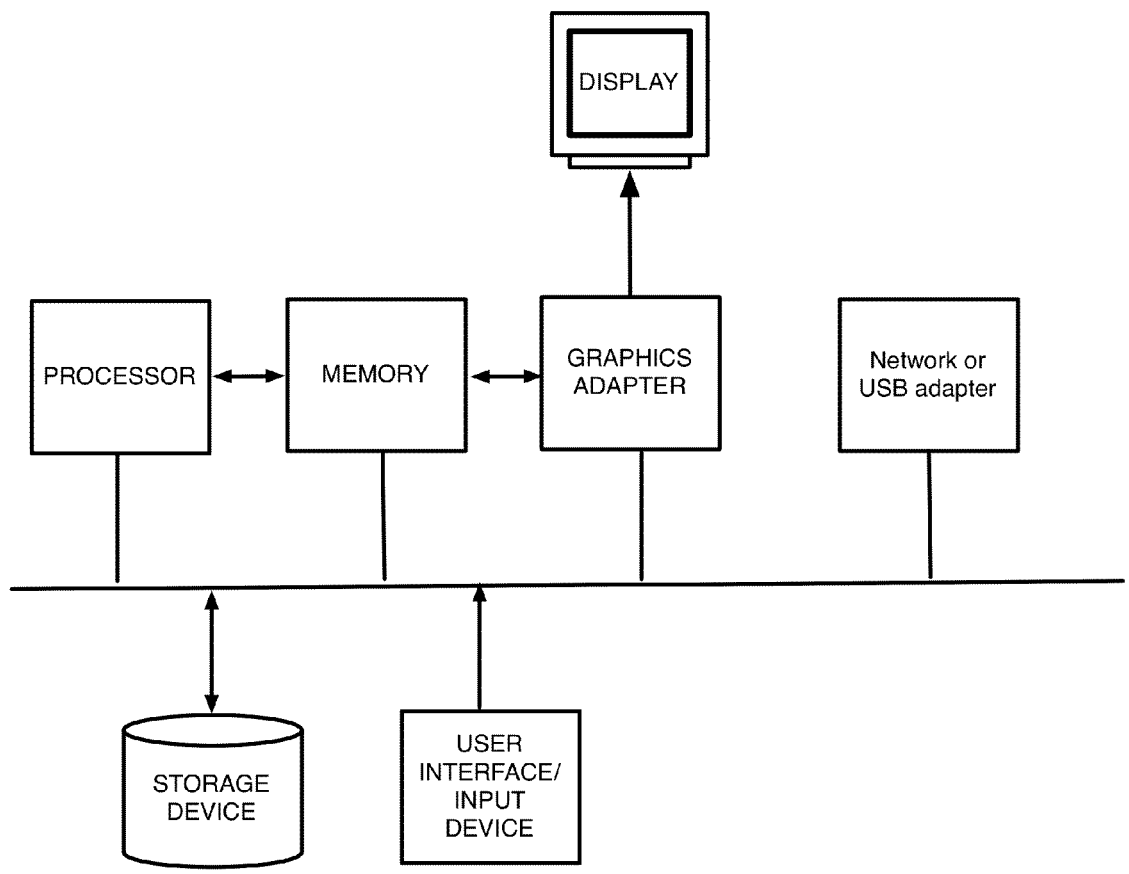
FIG. 11 illustrates a schematic diagram of a computer in the position determination system.

The magnetic sensors detect the magnetic filed information on the sensor planes in real time and send the magnetic filed data to the an external communication module. Communication module collects and processes the magnetic field information and further sends it a computer. Communication module includes a transmitter and transceiver nRFLE1 and nRFLU1, which is attached to a USB adapter of the computer. The magnetic data generated by the sensors on the sensor planes are processed and sent to the transceiver wirelessly and subsequently transferred to the computer through the USB adapter. The computer comprises at least a processor, memory, a graphic adapter and a storage device as shown in FIG. 10. The computer further comprises a display having a user interface.

The computer further comprises a mouse or user input device for example a touchscreen, allowing the user to point, select, search, close, for a file program, mage, open an icons. The user input device gives the user a full control of the computer system.

The display can be any kind of display suitable to display text and images. The display can be a plug-in display such as a computer monitor. Also it can be a display for a mobile device, such as a smart phone or tablet. The display has a user interface.

Figure 12:
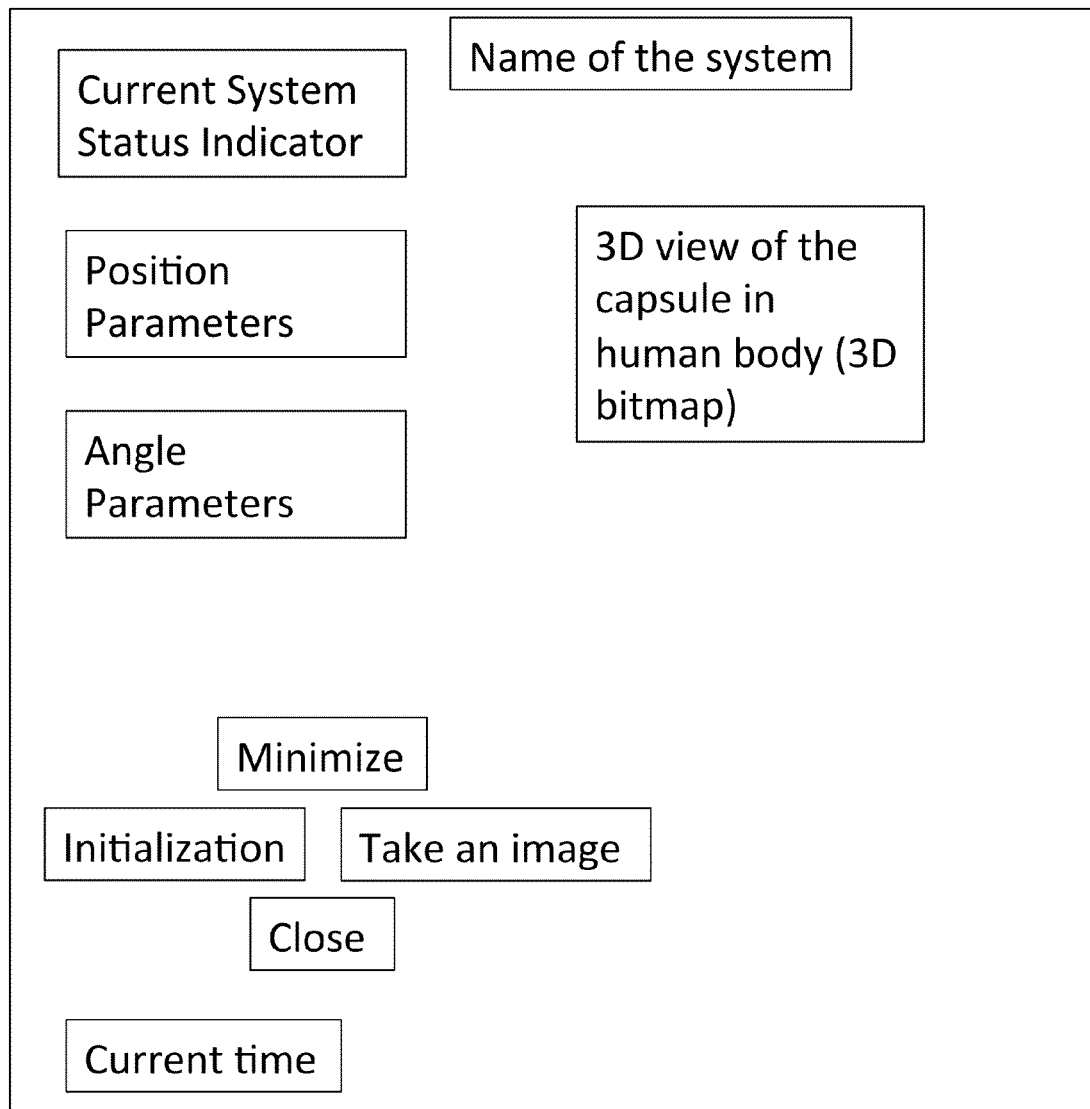
FIG. 12 illustrates a schematic diagram of a user interface.
Figure 13:
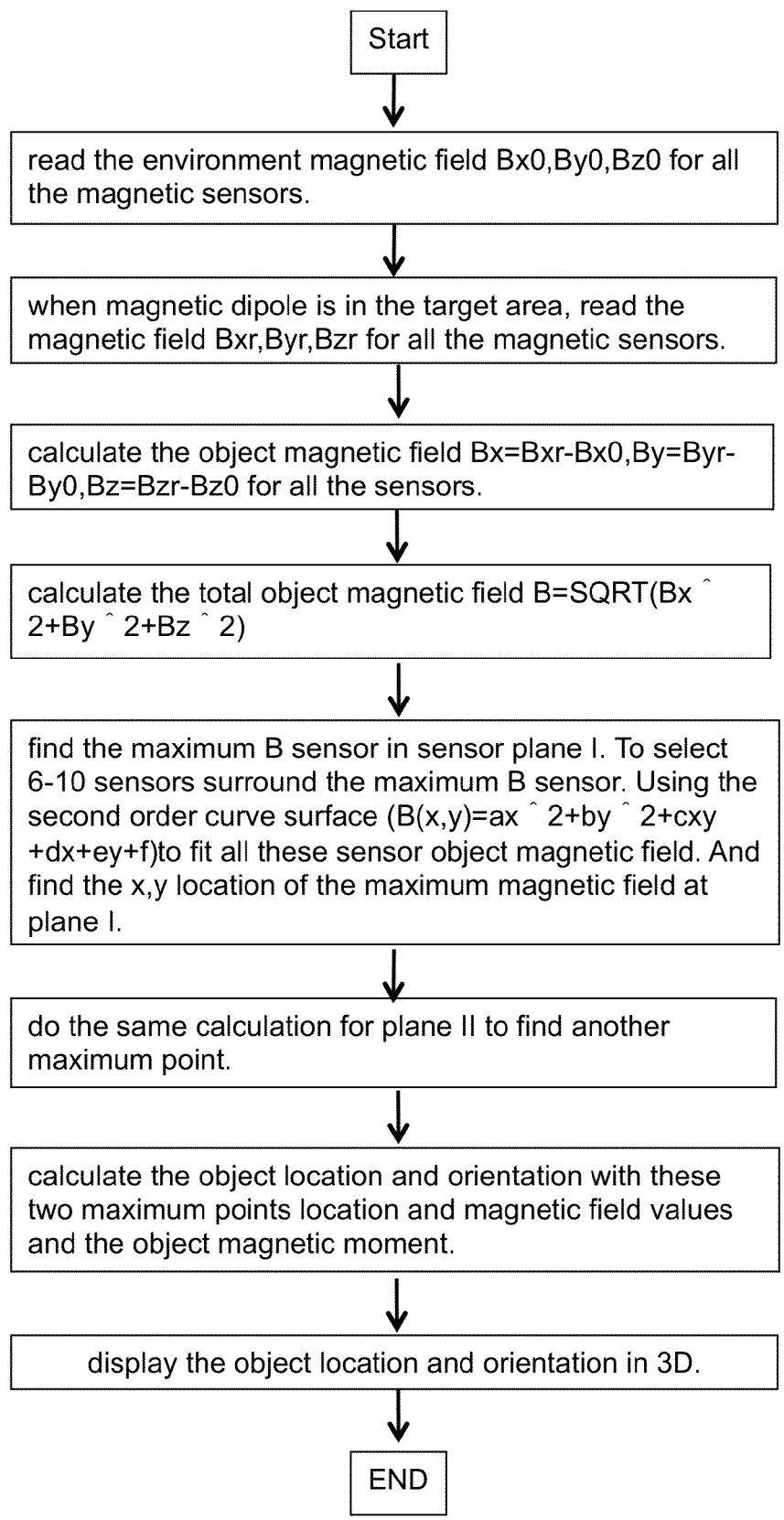
FIG. 13 is a flow diagram illustrating the steps to determine a location of a remote object, in accordance with the aspect with the present invention.

FIG. 12 shows an exemplary user interface of the computer, in accordance with the aspect of the present invention. On the top portion of the user interface, the name of the software is listed. For example, the name of "3-dimensional tracing systems for a capsule endoscope" is displayed as the first line of the user interface.

The user interface further comprises a current system status indicator module, capsule position parameters module and capsule angle parameter module. The current system status indicator module shows the status of the magnetic sensors on the sensor plane. In one example, the current system status indicator comprises ten LEDs, the LEDs are arranged correlating to the respective sensors in the magnetic sensor plane. LEDs use green and red colors to indicate the current status of the system. When the LED is Green, which means the corresponding magnetic sensor is ready to use or working properly. When the LED is Red, which means the corresponding sensor is either not working properly, or does not work.

Next to the current status indicator, said user interface comprises a capsule position parameter module and capsule angle parameter module. Position and angle parameter module displays the results of the current position (X, Y, Z) and angle parameters after calculating the capsule endoscope location and orientation in according to the detecting and calculation methods described herein. Positional parameters are displayed in centimeters and whereas angle parameters are displayed in degrees. The position parameters and angle parameters are display in association with a time and a target area information.

The capsule position parameter module and capsule angle parameter module are placed right next to an image module in the user interface. The image module displays a three-dimensional human body map as a reference environment. When a remote object having a permanent magnetic dipole, for example a magnetic capsule is detected by a sensor plane, the capsule is displayed in its appropriate position on the human body map. Further the capsulate displayed is in a three-dimensional view suggesting its location and pasture at the same time.

The user interface further includes control buttons such as initialization, minimization, and close buttons. Initialization button initialization the initial system, before locating the permanent magnetic diploe. Minimization button minimization the user interface and close button close the user interface.

The user interface further comprises image processing module, storage module and search module. Image processing module intercepts entire graphical interface, and storage module save them as BMP or JPG images.

The identification module receives the magnetic field information and calculates the position and orientation of the capsule and send the information to display unit for display.

The storage module also stores the position and orientation of remote permanent magnetic dipole and associated target area information from the identification module and assign a file name. The search module looks up the remote permanent magnetic dipole position data in response to a request of the file name.

The present invention disclosed herein is also directed to a computer implementable method of detecting a position and orientation of a capsule. The method includes reading an environment magnetic field along all three axes $Bx0, By0, Bz0$ for all magnetic sensors, placing a magnetic dipole in a target area and reading magnetic field data $Bxr, Byr, Bzr$ for all the magnetic sensors, calculating the object magnetic field using the equations $Bx=Bxr-Bx0, By=Byr-By0, Bz=Bzr-Bz0$ for all the sensors;

calculating the total object magnetic field according to the equation $B=SQRT(Bx^2+By^2+Bz^2)$ identifying a maximum magnetic field sensor (MB) on a first sensor plane;

selecting a group of 6-10 sensors surround the maximum magnetic field sensor (MB) and fitting the magnetic field data from the group of magnetic sensors using a second order curve surface $(B(x,y)=ax^2+by^2+cxy+dx+ey+f)$, and finding the x,y location of the maximum magnetic field at a first sensor plane;

performing the same calculation for a second sensor plane to find another maximum point, calculating the capsule location and orientation with the two maximum points location and magnetic field values and the object magnetic moment, and displaying the object location and orientation in a 3D view.

The present invention describes a system and method of determining a location and orientation of a remote permanent magnetic dipole. The embodiments and examples used herein are directed to a capsule, but this should not be interpreted as the limitation. The principles in the present invention can also be used for electric dipole detection and the electromagnetic dipole (example, RF dipole radiation) detection.

The systems and methods of the invention provide one or more advantages including but not limited to, providing accurate position determination for remote objects using measurements and analysis based on magnetic fields, increased efficiency, reduced costs. While the invention has been described with reference to certain illustrative embodiments, those described herein are not intended to be construed in a limiting sense. For example, variations or combinations of steps or materials in the embodiments shown and described may be used in particular cases without departure from the invention. Although the presently preferred embodiments are described herein in terms or planes and planar geometry, it is possible to practice the invention by substituting curved surfaces for planes, and adapting the calculations based on the selected curvature. Also, the computations described in terms of maximum values may be adapted to use minimum values or selected intermediate values without departure from the principles of the invention. These and other modifications and combinations of the illustrative embodiments as well as other advantages and embodiments of the invention will be apparent to persons skilled in the arts upon reference to the drawings, description, and claims.

We claim:

1. A system for locating a permanent magnetic dipole, comprising
    a permanent magnetic dipole adapted to be positioned in a target area;
    a non-stationary sensor plane, adapted to be positioned near the target area, the sensor plane comprising a plurality of magnetic sensors;
    a computer and computer executable program, comprising an identification module that identifies a position and orientation of the permanent magnetic dipole and an associated target area information in real time, wherein the dipole position is determined from a first maximum magnetic field of the dipole on the sensor plane in a first position P1 at time t1, and a second maximum magnetic field of the dipole on the sensor plane in a second position P2 at time t2, wherein a distance between centers of the sensor plane in P1 and P2 is at least 20 cm, and the dipole in the target area moves less than 10 mm in a time duration from t1 to t2, and wherein only one non-stationary sensor plane is used to determine the position of the permanent magnetic dipole and the position of the permanent magnetic dipole is calculated based on only the positions of the first and second maximum magnetic fields.

2. The position detection system of claim 1, further comprising a storage module that stores the position and orientation of the permanent magnetic dipole and associated target area information from the identification module and assigns a file name.

3. The position detection system of claim 2, wherein the storage module in the computer records time data associated with position and orientation data of the permanent magnetic dipole.

4. The position detection system of claim 1, further comprising a display unit that displays the position and orientation of the permanent magnetic dipole and associated target area information in a three-dimensional view.

5. The position detection system of claim 1, further comprising a mechanical arm attached to the sensor plane.

6. The position detection system of claim 5, wherein the mechanical arm is controlled by the computer.

7. The position detection system of claim 1, wherein the target area is an in vivo area inside a patient.

8. The position detection system of claim 7, wherein the first position and the second position are located on opposite sides of the patient.

9. A method for locating a permanent magnetic dipole, comprising
    providing a permanent magnetic dipole in a target area;
    placing a non-stationary sensor plane near the target area, wherein the sensor plane comprises a plurality of magnetic sensors,
    providing a computer operably coupled to the magnetic sensors,
    identifying a position and orientation of the permanent magnetic dipole and an associated target area information in real time, comprising the steps of placing the sensor plane to a first position P1 and recording its associated time t1,
    determining a first maximum magnetic field position of the permanent magnetic dipole when the sensor plane is in the first position P1;
    moving the sensor plane to a second position P2 and recording its associated time t2;
    determining a second maximum magnetic field position of the permanent magnetic dipole when the sensor plane is in the second position P2;
    and calculating the position of the permanent magnetic dipole using only the first and second maximum magnetic field positions;
    wherein only one sensor plane is used in the method, and a distance between centers of the sensor plane in P1 and P2 is at least 20 cm, and the dipole in the target area moves less than 10 mm in a time duration from t1 to t2.

10. The method of claim 9, further comprising storing the position and orientation of the permanent magnetic dipole and associated target area information from an identification module and assigning a file name.

* * * * *